United States Patent
Han et al.

(10) Patent No.: US 11,644,473 B2
(45) Date of Patent: May 9, 2023

(54) SERUM BIOMARKERS FOR PREDICTING AND EVALUATING RESPONSE TO TNF INHIBITOR THERAPY IN RHEUMATOID ARTHRITIS PATIENTS

(71) Applicant: ROWAN UNIVERSITY, Glassboro, NJ (US)

(72) Inventors: Kwanghoon Han, Cherry Hill, NJ (US); Andrea Bottaro, Cherry Hill, NJ (US); Nancy J. Olsen, Hershey, PA (US)

(73) Assignee: Rowan University, Glassboro, NJ (US)

( * ) Notice: Subject to any disclaimer, the term of this patent is extended or adjusted under 35 U.S.C. 154(b) by 1101 days.

(21) Appl. No.: 16/093,122

(22) PCT Filed: Apr. 14, 2017

(86) PCT No.: PCT/US2017/027668
§ 371 (c)(1),
(2) Date: Oct. 11, 2018

(87) PCT Pub. No.: WO2017/181038
PCT Pub. Date: Oct. 19, 2017

(65) Prior Publication Data
US 2021/0215712 A1    Jul. 15, 2021

Related U.S. Application Data

(60) Provisional application No. 62/323,260, filed on Apr. 15, 2016.

(51) Int. Cl.
*G01N 33/68* (2006.01)
*C07K 16/24* (2006.01)

(52) U.S. Cl.
CPC ....... *G01N 33/6893* (2013.01); *C07K 16/241* (2013.01); *C07K 2317/21* (2013.01); *G01N 2333/70578* (2013.01); *G01N 2333/7158* (2013.01); *G01N 2800/102* (2013.01); *G01N 2800/52* (2013.01)

(58) Field of Classification Search
None
See application file for complete search history.

(56) References Cited

U.S. PATENT DOCUMENTS

2011/0052488 A1* 3/2011 Dennis, Jr. ............. A61K 38/16
424/1.49

OTHER PUBLICATIONS

Waiker et al (J Am Soc Nephrol. Jan. 2012; 23(1): 13-21) (Year: 2012).*
Mayeux (NeuroRx. Apr. 2004;1(2):182-8) (Year: 2004).*
Ma (Modern Drug Discovery 2004, 7(6)) (Year: 2004).*
Steinman et al (Nat Med. Jan. 6, 2012;18(1):59-65) (Year: 2012).*
Blumberg et al (Nat Med.; 18(1): 35-41) (Year: 2015).*
Vajdos et al. (J Mol Biol. Jul. 5, 2002;320(2):415-28) (Year: 2002).*
Brown et al. (J Immunol. May 1996;156(9):3285-91) (Year: 1996).*
Guido et al (Curr Med Chem. 2008; 15(1):37-46) (Year: 2008).*
Clark et al (J. Med. Chem., 2014, 57 (12), pp. 5023-5038) (Year: 2014).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000,10:398-400) (Year: 2000).*
Souto-Caneiro (Arthritis Res Ther. 2009;11(3):R84. Epub Jun. 5, 2009) (Year: 2009).*
PeliKine Compact Human Soluble CD27 ELISA Kit Datasheet, [found online Jun. 6, 2017 at http://sanquin.pl/datasheet/m1960.pdf],Dec. 2005 ,pp. 1-11.
Souto-Carneiro, et al., Alterations in peripheral blood memory B cells in patients with active rheumatoid arthritis are dependent on the action of tumor necrosis factor, Arthritis Res & Ther, vol. 11. No. 3, R84 .2009 ,pp. 1-12.
PCT International Search Report & Written Opinion dated Jul. 21, 2017 for PCT International Application No. PCT/US2017/027668.

* cited by examiner

*Primary Examiner* — Brian Gangle
*Assistant Examiner* — Andrea K McCollum
(74) *Attorney, Agent, or Firm* — Saul Ewing LLP; Domingos J. Silva

(57) ABSTRACT

The present disclosure is directed to methods and kits for using serum biomarkers, including C-X-C Motif Chemokine Ligand 10 (CXCL10), C-X-C Motif Chemokine Ligand 13 (CXCL13), and/or soluble CD27 (sCD27), in predicting and evaluating therapeutic response to Tumor Necrosis Factor (TNF) inhibitor therapy in a patient in need thereof.

14 Claims, 6 Drawing Sheets

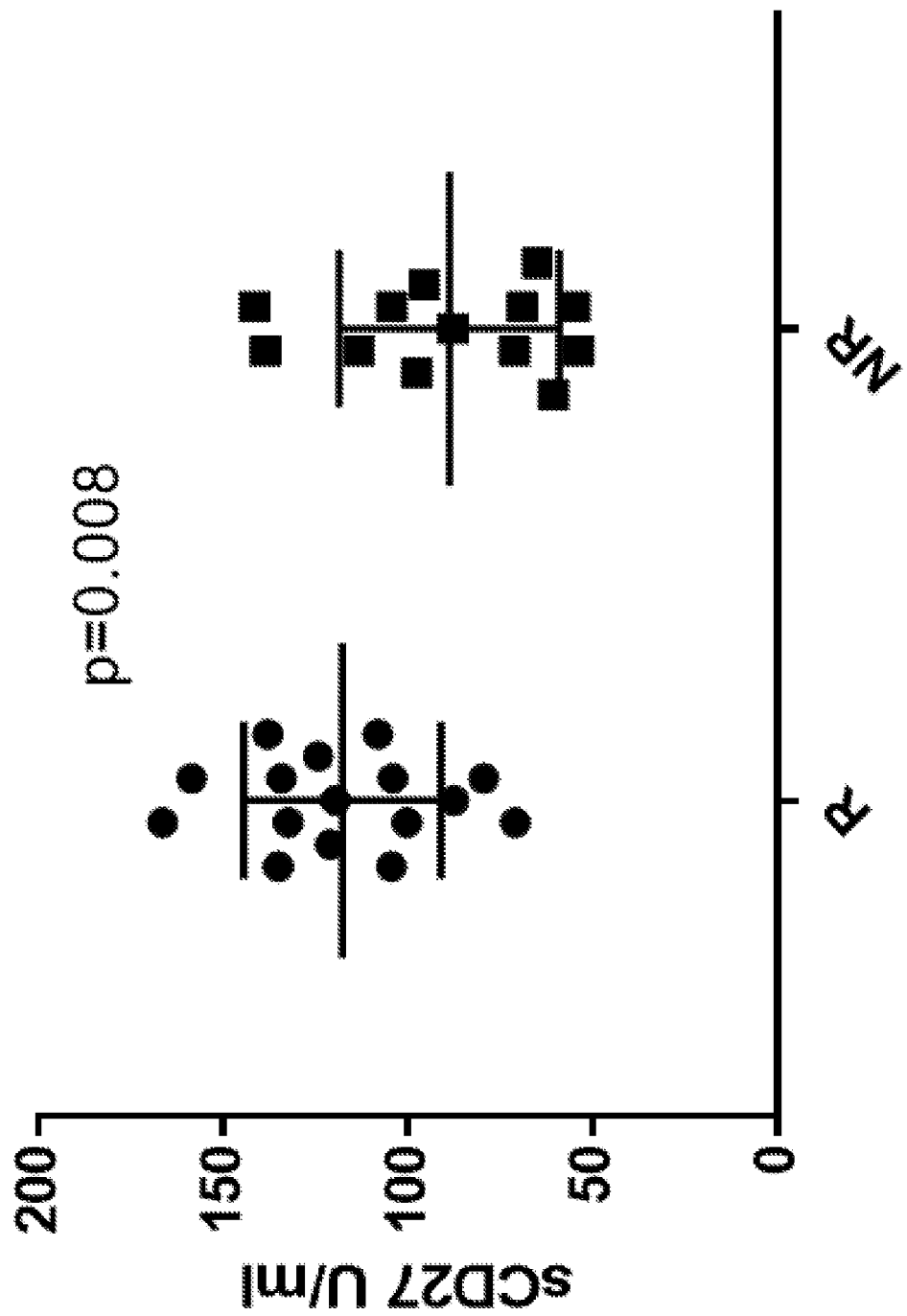

SERUM BIOMARKERS FOR PREDICTING AND EVALUATING RESPONSE TO TNF INHIBITOR THERAPY IN RHEUMATOID ARTHRITIS PATIENTS

CROSS-REFERENCE TO RELATED APPLICATIONS

This application is a 35 U.S.C. § 371 national phase application of, and claims priority to, International Application No. PCT/US2017/027668, filed Apr. 14, 2017, which claims priority under 35 U.S.C. § 119(e) to U.S. Provisional Patent Application No. 62/323,260, filed Apr. 15, 2016, all of which are incorporated herein by reference in their entireties.

FIELD OF THE INVENTION

The field of the invention is to use serum biomarkers, including CXCL10, CXCL13, and sCD27, for use in predicting and evaluating therapeutic response to TNF inhibitor therapy in rheumatoid arthritis patients.

BACKGROUND OF THE INVENTION

Rheumatoid arthritis (RA) is an autoimmune disease characterized by synovial inflammation, cartilage and bone destruction, and systemic features, as described in Firestein G S (2003) Nature; 423(6937):356-61 and Klareskog et al. (2008) Annu. Rev. Immunol.; 26:651-75, both references hereby incorporated by reference in their entireties. Advances in understanding the pathogenesis of the disease have fostered the development of new therapeutics. Tumor necrosis factor (TNF) inhibitors, for example the biologics adalimumab or etanercept, are used as a treatment for moderate to severe RA patients who have inadequate responses to conventional disease-modifying antirheumatic drugs (DMARDs) including methotrexate. However, reliable predictive biomarkers of therapeutic response for TNF inhibitor therapy are lacking. Accordingly, there is a need for identification of serum biomarkers for predicting therapeutic response to rheumatoid arthritis therapies, in particular TNF inhibitor therapy.

SUMMARY OF THE INVENTION

The present disclosure relates to the discovery that elevated baseline levels of three different serum biomarkers, CXCL10, CXCL13, and soluble CD27 (sCD27), in individuals who were diagnosed with rheumatoid arthritis (RA), were associated with favorable prognosis for treatment with TNF inhibitors. Accordingly, in some embodiments, the present disclosure is directed to a method of predicting a therapeutic response to TNF inhibitor therapy in a patient.

In some embodiments, the method comprises obtaining a biological sample from a patient. In some embodiments, the patient has been previously diagnosed with rheumatoid arthritis (RA). In some embodiments, the biological sample is obtained prior to treatment with a TNF inhibitor.

In some embodiments, the method comprises assaying the biological sample to determine a baseline serum level. In some embodiments, the baseline serum level is of CXCL10. In some embodiments, the baseline serum level of is CXCL13. In some embodiments, the baseline serum level is of sCD27. In some embodiments, the baseline serum level is of CXCL10 and of CXCL13. In some embodiments, the baseline serum level if of CXCL10, CXCL13, and of sCD27. In some embodiments, assaying the biological sample comprises contacting the biological sample with an antibody. In some embodiments, the antibody is an anti-CXCL10 antibody. In some embodiments, the antibody is an anti-CXCL13 antibody. In some embodiments, the antibody is an anti-CD27 antibody. In some embodiments, the assaying further comprises contacting the biological sample with anti-IgG antibodies. In some embodiments, the antibodies are labeled. In some embodiments, the label is a reporter molecule. In some embodiments, the label is an enzyme. In some embodiments, the enzyme is horseradish peroxidase. In some embodiments, the label is a fluorescent molecule. In some embodiments, the label is a radiolabel.

In some embodiments, the baseline serum level is compared to a reference serum level. In some embodiments, the reference serum level is of CXCL13. In some embodiments, the reference serum level is of CXCL10. In some embodiments, the reference level is of sCD27. In some embodiments, the reference serum level is generated from a population of individuals diagnosed with rheumatoid arthritis.

In some embodiments, the method comprises administering a TNF inhibitor to said patient. In some embodiments, the TNF inhibitor is administered to said patient if the baseline serum level is elevated relative to the reference serum level. In some embodiments, the TNF inhibitor is administered to said patient if the baseline serum level of CXCL10 is elevated relative to the reference level of CXCL10. In some embodiments, the TNF inhibitor is administered to said patient if the baseline serum level of CXCL13 is elevated relative to the reference level of CXCL13. In some embodiments, the TNF inhibitor is administered to said patient if the baseline serum level of CXCL10 and CXCL13 is elevated relative to the reference level of CXCL10 and CXCL13. In some embodiments, the TNF inhibitor is administered to said patient if the baseline serum level of sCD27 is elevated relative to the reference level of sCD27. In some embodiments, the TNF inhibitor is administered to said patient if the baseline serum level of CXCL10 and sCD27 is elevated relative to the reference level of CXCL10 and sCD27. In some embodiments, the TNF inhibitor is administered to said patient if the baseline serum level of CXCL13 and sCD27 is elevated relative to the reference level of CXCL13 and sCD27. In some embodiments, the TNF inhibitor is administered to said patient if the baseline serum level of CXCL10, CXCL13, and sCD27 is elevated relative to the reference level of CXCL10, CXCL13, and sCD27.

In some embodiments, the TNF inhibitor comprises adalimumab or an antigen-binding portion thereof. In some embodiments, the TNF inhibitor comprises a composition which is biosimilar to adalimumab. In some embodiments, the composition which is biosimilar to adalimumab comprises adalimumab-atto or an antigen-binding portion thereof. In some embodiments, the TNF inhibitor comprises certolizumab or an antigen-binding portion thereof. In some embodiments, the TNF inhibitor comprises certolizumab pegol. In some embodiments, the TNF inhibitor comprises a composition which is biosimilar to certolizumab. In some embodiments, the TNF inhibitor comprises etanercept. In some embodiments, the TNF inhibitor comprises a composition which is biosimilar to etanercept, comprising a TNF receptor fused to the constant region of an IgG1 antibody. In some embodiments, the composition which is biosimilar to etanercept comprises etanercept-szzs. In some embodiments, the TNF inhibitor comprises golimumab or an antigen-binding portion thereof. In some embodiments, the TNF inhibitor comprises a composition which is biosimilar to golimumab. In some embodiments, the TNF inhibitor comprises infliximab or an antigen-binding portion thereof. In some embodiments, the TNF inhibitor comprises a composition which is biosimilar to infliximab. In some embodiments, the composition which is biosimilar to infliximab comprises infliximab-dyyb.

In some embodiments, a disease-modifying antirheumatic drug (DMARD) is additionally administered to said patient. In some embodiment, the DMARD is selected from the group consisting of hydroxychloroquine sulfate, leflunomide, methotrexate, sulfasalazine, and combinations thereof. In some embodiments, the DMARD is additionally administered with an anti-inflammatory compound. In some embodiments, the anti-inflammatory compound comprises a non-steroidal anti-inflammatory drug (NSAID).

The present disclosure is additionally directed to a method of evaluating a therapeutic response to TNF inhibitor therapy in a patient. In some embodiments, the method comprises obtaining a first biological sample from a patient. In some embodiments, the patient has been previously diagnosed with rheumatoid arthritis (RA). In some embodiments, the first biological sample is obtained prior to treatment with a TNF inhibitor.

In some embodiments, the method comprises assaying the first biological sample to determine a baseline serum level. In some embodiments, the baseline serum level is of CXCL10. In some embodiments, the baseline serum level of is CXCL13. In some embodiments, the baseline serum level is of sCD27. In some embodiments, the baseline serum level is of CXCL10 and of CXCL13. In some embodiments, the baseline serum level if of CXCL10, CXCL13, and of sCD27. In some embodiments, assaying the first biological sample comprises contacting the first biological sample with an antibody. In some embodiments, the antibody is an anti-CXCL10 antibody. In some embodiments, the antibody is an anti-CXCL13 antibody. In some embodiments, the antibody is an anti-CD27 antibody. In some embodiments, the assaying further comprises contacting the first biological sample with anti-IgG antibodies. In some embodiments, the antibodies are labeled. In some embodiments, the label is a reporter molecule. In some embodiments, the label is an enzyme. In some embodiments, the enzyme is horseradish peroxidase. In some embodiments, the label is a fluorescent molecule. In some embodiments, the label is a radiolabel.

In some embodiments, after assaying the first biological sample, the method comprises administering a TNF inhibitor to said patient. In some embodiments, the TNF inhibitor comprises adalimumab or an antigen-binding portion thereof. In some embodiments, the TNF inhibitor comprises a composition which is biosimilar to adalimumab. In some embodiments, the composition which is biosimilar to adalimumab comprises adalimumab-atto or an antigen-binding portion thereof. In some embodiments, the TNF inhibitor comprises certolizumab or an antigen-binding portion thereof. In some embodiments, the TNF inhibitor comprises certolizumab pegol. In some embodiments, the TNF inhibitor comprises a composition which is biosimilar to certolizumab. In some embodiments, the TNF inhibitor comprises etanercept. In some embodiments, the TNF inhibitor comprises a composition which is biosimilar to etanercept, comprising a TNF receptor fused to the constant region of an IgG1 antibody. In some embodiments, the composition which is biosimilar to etanercept comprises etanercept-szzs. In some embodiments, the TNF inhibitor comprises golimumab or an antigen-binding portion thereof. In some embodiments, the TNF inhibitor comprises a composition which is biosimilar to golimumab. In some embodiments, the TNF inhibitor comprises infliximab or an antigen-binding portion thereof. In some embodiments, the TNF inhibitor comprises a composition which is biosimilar to infliximab. In some embodiments, the composition which is biosimilar to infliximab comprises infliximab-dyyb.

In some embodiments, the method comprises administering the TNF for a period of time. In some embodiments, the period of time is less than 1 month, about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months or greater than 24 months, or any intervening ranges.

In some embodiments, the method comprises obtaining a second biological sample after said period of time. In some embodiments, the method comprises assaying the second biological sample to determine a treatment serum level. In some embodiments, the treatment serum level is of CXCL10. In some embodiments, the treatment serum level of is CXCL13. In some embodiments, the treatment serum level is of sCD27. In some embodiments, the treatment serum level is of CXCL10 and of CXCL13. In some embodiments, the treatment serum level if of CXCL10, CXCL13, and of sCD27. In some embodiments, assaying the second biological sample comprises contacting the second biological sample with an antibody. In some embodiments, the antibody is an anti-CXCL10 antibody. In some embodiments, the antibody is an anti-CXCL13 antibody. In some embodiments, the antibody is an anti-CD27 antibody. In some embodiments, the assaying further comprises contacting the second biological sample with anti-IgG antibodies. In some embodiments, the antibodies are labeled. In some embodiments, the label is a reporter molecule. In some embodiments, the label is an enzyme. In some embodiments, the enzyme is horseradish peroxidase. In some embodiments, the label is a fluorescent molecule. In some embodiments, the label is a radiolabel.

In some embodiments, the method comprises comparing the baseline serum level with the treatment serum level. In some embodiments, the method comprises continuing administration of a TNF inhibitor to said patient. In some embodiments, administration of a TNF inhibitor to said patient is continued if the baseline serum level is elevated relative to the treatment serum level. In some embodiments, administration of a TNF inhibitor to said patient is continued if the baseline serum level of CXCL10 is elevated relative to the treatment level of CXCL10. In some embodiments, administration of a TNF inhibitor to said patient is continued if the baseline serum level of CXCL13 is elevated relative to the treatment serum level of CXCL13. In some embodiments, administration of a TNF to said patient is continued if the baseline serum level of CXCL10 and CXCL13 is elevated relative to the treatment level of CXCL10 and CXCL13. In some embodiments, administration of a TNF inhibitor to said patient is continued if the baseline serum level of sCD27 is elevated relative to the treatment level of sCD27. In some embodiments, administration of a TNF inhibitor to said patient is continued if the baseline serum level of CXCL10 and sCD27 is elevated relative to the treatment level of CXCL10 and sCD27. In some embodiments, administration of a TNF inhibitor to said patient is continued if the baseline serum level of CXCL13 and sCD27 is elevated relative to the treatment level of CXCL13 and sCD27. In some embodiments, administration of a TNF to said patient is continued if the baseline serum level of CXCL10, CXCL13, and sCD27 is elevated relative to the treatment level of CXCL10, CXCL13, and sCD27.

In some embodiments, a disease-modifying antirheumatic drug (DMARD) is additionally administered to said patient. In some embodiment, the DMARD is selected from the group consisting of hydroxychloroquine sulfate, leflunomide, methotrexate, sulfasalazine, and combinations thereof. In some embodiments, the DMARD is additionally administered with an anti-inflammatory compound. In some embodiments, the anti-inflammatory compound comprises a non-steroidal anti-inflammatory drug (NSAID).

BRIEF DESCRIPTION OF THE FIGURES

FIG. 2 represents baseline serum chemokine levels in responders (n=16) and non-responders (n=13) to TNF inhibitor therapy.

FIG. 3 represents that baseline CXCL10 and CXCL13 levels predict response to TNF inhibitor therapy.

FIG. 4 represents baseline serum chemokine levels of sCD27 in responders (n=15) and non-responders (n=13) to TNF inhibitor therapy.

DETAILED DESCRIPTION OF THE INVENTION

Figure 1:
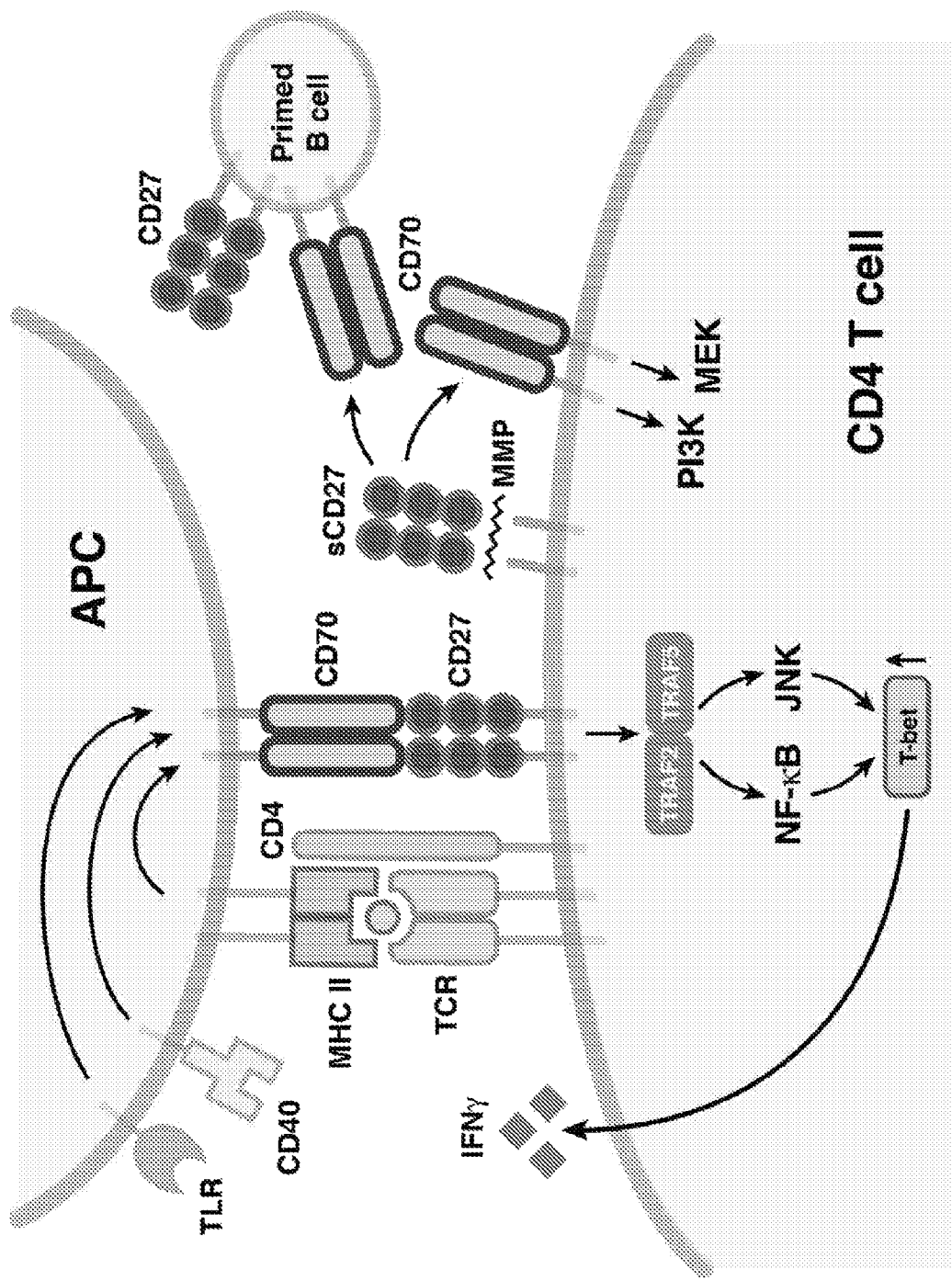
FIG. 1 represents the CD27-CD70 pathway in immune regulation.

The present disclosure relates to the discovery that elevated baseline levels of three different serum biomarkers, CXCL10, CXCL13, as shown in Example 1 infra, and soluble CD27 (sCD27), as shown in Example 2 infra, in individuals who were diagnosed with rheumatoid arthritis (RA), were associated with favorable prognosis for treatment with TNF inhibitors. Thus the present disclosure is directed primarily to methods of predicting a therapeutic response to TNF inhibitor therapy in a patient as well as methods of evaluating a therapeutic response to TNF inhibitor therapy in a patient.

In the first aspect (predicting a therapeutic response), the method generally comprises obtaining a biological sample from a patient who has been previously diagnosed as having rheumatoid arthritis (RA), preferably prior to the patient having started a TNF inhibitor therapy, assaying the biological sample to determine a baseline serum level of one or more serum biomarkers, including (but not limited to) CXCL10, CXCL13, and/or sCD27, as well as various combinations of those serum biomarkers, comparing the baseline serum level of CXCL10, CXCL13, and/or sCD27, or various combinations of CXCL10, CXCL13, and/or sCD27 with reference serum levels of CXCL10, CXCL13, and/or sCD27, or various combinations thereof, and based on the results of comparing the baseline serum levels with the reference serum levels, starting the patient on a TNF inhibitor regimen (i.e. administering to the patient a TNF inhibitor).

The patient baseline serum levels of CXCL10, CXCL13 and/or sCD27 are compared to reference serum levels of the same factors. Optionally, a "score" is generated based on calculated specificity and sensitivity, as to the probability that a patient will respond to TNF inhibitor, such as described in Example 4 infra. This score would be utilized to guide clinical decision-making with regard to treatment. The reference levels of CXCL10, CXCL13, and/or sCD27 are derived from a population of individuals, preferably from individuals who have already been diagnosed with rheumatoid arthritis, although not necessarily, as the reference levels of CXCL10, CXCL13, and/or sCD27 may be obtained from a general population. The reference levels may include further selective criteria, such as age, sex, severity of the disease, previous treatment with either TNF inhibitors and/or DMARDs, and other conditions, such as other autoimmune or connective tissue disorders. Non-limiting examples of inclusion and exclusion criteria are presented in Examples 1 and 2 infra.

Typically, if the baseline levels of CXCL10, CXCL13, and/or sCD27 are elevated relative to the reference levels of CXCL10, CXCL13, and/or sCD27, the patient is then started on a TNF inhibitor regimen. This is because, as disclosed herein, elevated levels of CXCL10, CXCL13, and sCD27 are, individually and in combination, predictive of increased responsiveness to TNF inhibitor therapy in individuals who have been diagnosed with rheumatoid arthritis. This means that patients who have elevated baseline levels of CXCL10, CXCL13, and/or sCD27 will likely benefit from TNF inhibitor therapy relative to those individuals who do not have elevated baseline levels of CXCL10, CXCL13, and/or sCD27. Individuals diagnosed with RA who have elevated levels of both CXCL10 and CXCL13 are shown in Example 1 infra to be responsive to TNF inhibitor therapy, and individuals diagnosed with RA who have elevated levels of sCD27 were shown in Example 2 infra to be responsive to TNF inhibitor therapy. Reference serum levels for CXCL10, CXCL13, and sCD27 will vary depending on the patient population tested. For example, median values of serum CXCL10, CXCL13 and sCD27 levels in RA patients from Examples 1 and 2 infra were 260 pg/mL, 50 pg/mL, and 96 U/mL respectively. However these results are expected to vary. In addition to treatment with TNF inhibitor therapy, the patient may receive treatment with one or more DMARDs as disclosed herein.

In the second aspect (evaluating a therapeutic response), the method generally comprises obtaining a first biological sample from a patient who has been previously diagnosed as having rheumatoid arthritis (RA), preferably prior to the patient having started TNF inhibitor therapy, assaying the first biological sample to determine a baseline serum level of one or more serum biomarkers, including (but not limited to) CXCL10, CXCL13, and/or sCD27, as well as various combinations of those serum biomarkers, starting the patient on a TNF inhibitor therapy (i.e. administering a TNF inhibitor to the patient) for a period of time, obtaining a second biological sample from the patient after said period of time, assaying the second biological sample to determine a treatment serum level of one or more serum biomarkers, including (but not limited to) CXCL10, CXCL13, and/or sCD27, as well as various combinations of those serum biomarkers, comparing the baseline serum levels with the treatment serum levels, and based on the results of comparing the baseline serum levels with the treatment serum levels, continuing the patient on a TNF inhibitor (which may or may not be the same TNF inhibitor or combination of TNF inhibitors as was administered for the first period of time).

The period of time between when the TNF inhibitor therapy is started (i.e. when first administering the TNF inhibitor to the patient) and when the second biological sample is taken may range depending on clinical indication, but typically is between about 1 month and about 24 months, more typically between about 1 month and about 6 months. For example, serum levels of CXCL10 and CXCL13 were taken at 14 weeks in Example 1 infra and serum levels of sCD27 were taken at 14 weeks in Example 2 infra.

Therefore, the period of time may be less than about 1 months, about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, or more than about 24 months, and any intervening range therein, for example, about 1-2 months, about 1-3 months, about 1-4 months, about 1-5 months, about 1-6 months, about 1-7 months, about 1-8 months, about 1-9 months, about 1-10 months, about 1-11 months, about 1-12 months, about 1-13 months, about 1-14 months, about 1-15 months, about 1-16 months, about 1-17 months, about 1-18 months, about 1-19 months, about 1-20 months, about 1-21 months about 1-22 months about 1-23 months, about 1-24 months, about 2-3 months, about 2-4 months, about 2-5 months, about 2-6 months, about 2-7 months, about 2-8 months, about 2-9 months, about 2-10 months, about 2-11 months, about 2-12 months, about 2-15 months, about 2-24 months, about 3-4 months, about 3-5 months, about 3-6 months, about 3-7 months, about 3-8 months, about 3-9 months, about 3-10 months, about 3-11 months, about 3-12 months, about 4-5 months, about 4-6 months, about 4-12 months, about 4-24 months, about 5-10 months, about 6-12 months, about 10-12 months, about 10-15 months, about 10-24 months, about 12-15 months, about 12-24 months, and any intervening ranges therein.

Both the baseline serum levels and the treatment serum levels of CXCL10, CXCL13, and/or sCD27 in this aspect are taken from the individual from who the TNF inhibitor therapy is being administered to. Typically, if the baseline levels of CXCL10, CXCL13, and/or sCD27 are elevated relative to the treatment levels of CXCL10, CXCL13, and/or sCD27, the patient is then continued on a TNF inhibitor regimen. This is because, without wishing to be bound by theory, a reduction in levels of CXCL10, CXCL13, and/or sCD27 from the baseline serum levels relative to the treatment serum levels in an individual who has been receiving a TNF inhibitor is indicative of responsiveness to the TNF inhibitor and an overall positive prognosis for continued treatment with a TNF inhibitor. In addition to treatment with TNF inhibitor therapy, the patient may receive treatment with one or more DMARDs as disclosed herein.

It is possible, and may be desirable in some instances, to combine the first aspect (predicting a therapeutic response) with the second aspect (evaluating a therapeutic response). In such instances, this would generally comprise a method comprising taking a first biological sample from a patient who has been previously diagnosed as having rheumatoid arthritis (RA), preferably prior to the patient having started TNF inhibitor therapy, assaying the first biological sample to determine a baseline serum level of one or more serum biomarkers, including (but not limited to) CXCL10, CXCL13, and/or sCD27, as well as various combinations of those serum biomarkers, comparing the baseline serum levels with reference serum levels of CXCL10, CXCL13, and/or sCD27, as well as various combinations of those serum biomarkers, starting the patient on a TNF inhibitor regimen (i.e. administering to the patient a TNF inhibitor) for a period of time, obtaining a second biological sample from the patient after said period of time, assaying the second biological sample to determine a treatment serum level of one or more serum biomarkers, including (but not limited to) CXCL10, CXCL13, and/or sCD27, as well as various combinations of those serum biomarkers, comparing the baseline serum levels with the treatment serum levels, and/or potentially with the reference serum levels again, and based on the results of comparing the baseline serum levels with the treatment and/or reference serum levels, continuing the patient on a TNF inhibitor (which may or may not be the same TNF inhibitor or combination of TNF inhibitors as was administered for the first period of time).

Assaying any of the various biological samples in any of the aspects of the present disclosure may occur by any known means in the art, for example, by immunoassay. By way of example, enzyme linked immunosorbent (ELISA) assays were used in Examples 1 and 2 infra to quantify the amount of serum biomarker present. Other immunoassays may include enzyme immune assays (EIA), ELISPOT (enzyme-linked immunospot), radioimmunoassays (RIAs), immunofluorescence, and other assays known in the art, including but not limited to Western Blot analysis and/or immunoprecipitation methods.

For example in a direct ELISA, a buffered solution of an antigen, e.g. a biological sample containing CXCL10, CXCL13, and/or sCD27, is added to a well of a microtiter plate, e.g. a 96-well plate, A solution of non-reacting protein, e.g. bovine serum albumin or casein is then added to the well. Anti-CXCL10, anti-CXCL13, and/or anti-CD27 antibody or antigen-binding portions thereof, typically conjugated to a reporter molecule enzyme is added, e.g. conjugated to horse-radish peroxidase, although that is not necessarily the enzyme, as other common enzymes include alkaline phosphatase, or β-D-galactosidase, although other enzymes are conceivable and considered embodied by this disclosure. A substrate for the enzyme is then added, which leads to a detectable signal. For example, adding TMB to horseradish peroxidase leads to a colored product, in which case the ELISA is a colorimetric assay. ELISAs may be run in a qualitative or quantitative format. Qualitative results provide a simple positive or negative result (yes or no) for a sample. The cutoff between positive and negative is determined by an analyst and may be statistical. Sandwich ELISAs generally follow the following protocol. Capture anti-CXCL10, anti-CXCL13, and/or anti-CD27 antibodies are immobilized on a substrate, e.g. a microtiter plate. Antigen-containing sample is then added to the substrate at which point it is captured by the antibodies. The substrate is then washed to remove unbound antigen. Detecting anti-CXCL10, anti-CXCL13, and/or anti-CD27 antibodies is then added, which bind to different epitope(s) on CXCL10, CXCL13, and/or sCD27 than the bound anti-CXCL10, anti-CXCL13, and/or anti-CD27 antibodies. The detecting antibodies may be bound to a reporter molecule, e.g. an enzyme, although the reporter molecule may be any molecule which leads to a detectable signal. Alternatively, a secondary antibody that is specific to the detecting antibody, for example (but not necessarily), anti-IgG antibodies, are added. The secondary antibody is often bound to a label, such as reporter molecule or an enzyme (or any other molecule that may lead to a detectable signal). The plate may be washed an additional time prior to adding in secondary antibody, and in those instances where the reporter molecule is an enzyme, a substrate may be added, e.g. TMB, that results in a detectable signal (also a colorimetric assay). A third type of common ELISA is competitive ELISA. In these embodiments, unlabeled anti-CXCL10, anti-CXCL13, and/or anti-CD27 antibodies incubated in the presence of an antigen-containing sample (e.g. a biological sample) which are then added to an antigen-coated well. The plate is washed so as to remove unbound antibodies. A secondary antibody that is specific to the primary antibody, for example (but not necessarily), anti-IgG antibodies, are added. The secondary antibody is bound to a label, such as reporter molecule or an enzyme (or any other molecule that may lead to a detectable signal). Some competitive ELISA utilize labeled antigens rather than labeled antibodies; the less antigen in the sample, the more labeled antigen is retained and the stronger a detectable signal results.

Other forms of common in vitro assays include radioimmunoassays (RIAs). Typically a known quantity of an antigen is linked to a radioactive tracer, e.g. 1-125 although others are suitable for use, which is then mixed with a known amount of antibody specific for the antigen, e.g. anti-CXCL10, anti-CXCL13, and/or anti-CD27 antibodies. Then, a sample containing unknown quantity of an antigen is added. This is a direct competitive measurement for specific binding; as the concentration of unlabeled antigen is increased, the binding between the antibodies and the labeled standard is decreased, which is directly measurable by measuring radioactivity. Other assays are known and a person of ordinary skill in the art would readily recognize their applicability.

As used herein, "adalimumab" refers to the FDA-approved human monoclonal antibody that specifically binds to tumor necrosis factor (TNF), as well as any biosimilar monoclonal antibodies or antigen-binding portions thereof, for example, but limited to, adalimumab-atto. Adalimumab was the first fully human, recombinant IgG1 anti-TNF monoclonal antibody, having high selectivity and affinity for TNF as described in, for example, Mease P (2007) Ther. Clin. Risk Manag. 3(1) 133-148, hereby incorporated by reference in its entirety.

As used herein, "antibody" (Ab) as used herein is used in the broadest sense and specifically may include any immunoglobulin, whether natural or partly or wholly synthetically produced, including but not limited to monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2a, IgG2b, IgG3, IgG4, IgM, IgA1, IgA2, IgD, and IgE) and biologically relevant fragment or specific binding member thereof, including but not limited to Fab, F(ab')2, scFv (single chain or related entity) and (scFv)$_2$. The term "antibody fragments" as used herein may include those antibody fragments obtained using techniques readily known and available to those of ordinary skill in the art, as reviewed herein. Therefore, in addition to the definition for "antibody" presented supra, the term "antibody" may further encompass any polypeptide or protein comprising a portion of an intact antibody, such as the antigen binding or variable region of the intact antibody. These can be derived from natural sources, or they may be partly or wholly synthetically produced. Examples of antibody fragments include, but are not limited to, Fab, Fab', F(ab')2, and Fv fragments; diabodies, and linear antibodies.

As used herein, the term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), bodily fluids, lavages, pancreatic juices, gastric juices, discharges, CSF, lymph amniotic fluid, plasma, semen, bone marrow, and tissue or fine needle biopsy samples, urine, stool, peritoneal fluid, and pleural fluid, or cells therefrom, and any combinations thereof. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, "CD27" refers to the member of the tumor necrosis factor receptor superfamily that binds to the ligand CD70. As used herein, "sCD27" refers to soluble CD27. As illustrated in Example 2 infra, sCD27 is predictive serum biomarker, alongside CXCL10 and CXCL13, which can serve in evaluating a response to TNF inhibitor therapy in patients suffering from rheumatoid arthritis (RA). CD27 and CD70 are ligand-counter ligand pair that has been recognized as providing stimulatory signals for T cell and B cell activation, for example, as disclosed in Lens et al. (1998) Semin. Immunol.; 10: 491-9, Agematsu et al. (2000) Immunol. Today; 21: 204-6, and Croft, M. (2003) Nat. Rev. Immunol.; 3: 609-20, each hereby incorporated by reference in its entirety. CD27 (TNFRSF7) belongs to the tumor necrosis factor (TNF) receptor family and is found on, for example, CD4+ and CD8+T lymphocytes, natural killer (NK) cells and hematopoietic stem cells, as described in Agematsu et al. (2000), Tortorella et al. (1995) J. Immunol.; 155: 149-62, Jacquot et al. (1997) J. Immunol.; 159: 2652-7, Hintzen et al. (1994) Int. Immunol.; 6: 477-80, Yang et al. (1996) Immunology; 88: 289-93, Takeda et al. (2000) J. Immunol.; 164: 1741-5, and Wiesmann et al. (2000) Immunity; 12: 193-9, each hereby incorporated by reference in its entirety. CD27 is not expressed by naïve B lymphocytes, but is upregulated in activated and antigen-experienced B lymphocytes, as described by Xiao et al. (2004) Immunol.; 172: 7432-41, hereby incorporated by reference in its entirety. Soluble CD27 (sCD27) can be cleaved from the membrane bound form on activated T lymphocytes through the action of matrix metalloproteinase, as disclosed in Loenen et al. (1992) Eur. J. Immunol.; 22: 447-55, hereby incorporated by reference in its entirety. The only characterized ligand of CD27 is CD70 (TNFSF7), a TNF superfamily member expressed on activated T lymphocytes, B lymphocytes, dendritic cells and NK cells, and also weakly on activated macrophages, as disclosed in Tortorella et al. (1995), Tesselaar et al. (2003) J. Immunol.; 170: 33-40 and Kashii et al. (1999) J. Immunol.; 163: 5358-66, each reference hereby incorporated by reference in its entirety. Thus, the CD27-CD70 interaction is primarily regulated by expression of CD70, which is induced by Toll like receptor (TLR), CD40 and/or antigen receptor signaling, as described in Tesselaar et al. (2003) and Sanchez et al. (2007) J. Immunol.; 178: 1564-72, hereby incorporated by reference in its entirety. Similarly to other TNF family members (e.g., CD40L), CD70 is capable of retrograde signaling, as described in Garcia et al. (2004) J. Keukoc. Biol.; 76: 263-70 and Arens et al. (2004) J. Immunol.; 173: 3901-8, both references hereby incorporated by reference in their entireties. CD27-CD70 interactions have bi-directional functional effects as illustrated in FIG. 1.

As used herein, "certolizumab" or "certolizumab pegol" refers to the FDA-approved humanized monoclonal antibody fragment that specifically binds to tumor necrosis factor (TNF), as well as any biosimilar antibody fragments or antigen-binding portions thereof. Certolizumab is a PEGylated Fab' fragment of a humanized TNF inhibitor monoclonal antibody. Use of certolizumab to treat rheumatoid arthritis is described in, for example, Patel et al. (2010) Expert Rev Clin Immunol.; 6(6) 855-866, hereby incorporated by reference in its entirety.

As used herein, "CXCL10" refers to C-X-C motif chemokine 10. As illustrated in Example 1 infra, subjects diagnosed with rheumatoid arthritis (RA) who have elevated baseline serum levels of CXCL10 may represent a subset of RA patients whose inflammatory reactions are primarily driven by TNF, and thus may benefit from treatment comprising a TNF inhibitor, for example, adalimumab or etanercept. CXCL10 is induced by type I and II IFNs as described in Luster et al. (1987) J Exp Med; 166(4):1084-97 and Ciche et al. (2014) Arthritis Rheumatol.; 66(6):1583-95, both references hereby incorporated by reference in their entireties, as well as TNF as disclosed in Ohmori et al. (1993) Am J Pathol.; 142(3):861-70, hereby incorporated by reference in its entirety, and has been evaluated as a surrogate biomarker to reflect the IFN signature upregulated in autoimmune rheumatic diseases including RA and systemic lupus erythematosus (SLE), as described in Karonitsch et al. (2012) Arthritis Rheum.; 64(2):400-8 and Rose et al. (2013) Ann Rheum Dis.; 72(10):1639-45, both references hereby incorporated by reference in their entireties. Eriksson et al. (2013) Scand J Rheumatol.; 42(4):260-5, hereby incorporated by reference in its entirety, illustrated that infliximab therapy leads to significant decrease in serum CXCL10 levels in RA patients, which is consistent with Example 1. Eriksson et al. showed CXCL10 levels decreased with infliximab therapy but did not assess if baseline CXCL10 levels predicted the response to TNF inhibitor therapy. Of note, RA patients with high baseline type I IFN activity have a good response to TNF inhibitors, as shown in Mavragani et al. (2010) Arthritis Rheum.; 62(2):392-401, hereby incorporated by reference in its entirety. Additionally, it has been reported that type I IFN signature is induced by TNF in RA patients in Gordon et al. (2012) Arthritis Rheum.; 64(10): 3119-28, hereby incorporated by reference in its entirety. CXCR3-expressing Th1 lymphocytes and monocytes recruited by CXCL10 secrete TNF in RA as described in Antonelli et al. (2008) Autoimmun. Rev.; 8(1):18-23 and Lee et al. (2013) Autoimmun. Rev.; 12(5):554-7, both references hereby incorporated by reference in their entireties. Furthermore, TNF induces type I IFN synthesis by macrophages and fibroblast-like synoviocytes, which in turn stimulates CXCL10 secretion in an autocrine manner and creates a positive feedback loop, as described in Yarilina et al. (2008) Nat Immunol.; 9(4):378-87 and in Rosengren et al. (2012) Ann Rheum Dis.; 71(3):440-7, both references hereby incorporated by reference in their entireties. In this regard, CXCL10 may be used as a marker associated with both TNF and type I IFN pathways, which are closely linked to each other in RA. Example 1 infra provides additional evidence in support of the above notion. Additional methods for detecting CXCL10 are disclosed in, for example, WO 2016/177791, hereby incorporated by reference in its entirety.

As used herein, "CXCL13" refers to C-X-C motif chemokine 13. As illustrated in Example 1 infra, subjects diagnosed with rheumatoid arthritis (RA) who have elevated baseline serum levels of CXCL13, like those with elevated baseline levels of CXCL10, may represent a subset of RA patients whose inflammatory reactions are primarily driven by TNF, and thus may benefit from treatment comprising a TNF inhibitor, for example, adalimumab or etanercept. CXCL13 is constitutively expressed by follicular dendritic cells and is involved in formation of secondary lymphoid tissues in RA, as described in Shi et al. (2001) J Immunol; 166(1):650-5, hereby incorporated by reference in its entirety. Additionally, it is upregulated in a subset of T cells by T cell receptor engagement and by TNF or IL-6 as described in Manzo et al. (2008) Arthritis Rheum.; 58(11): 3377-87 and Kobayashi et al. (2013) Arthritis Rheum.; 65(12):3063-72, as well as in macrophages as described in Carlsen et al. (2004) Blood.; 104(10): 3021-7, all references incorporated by reference in their entireties. CXCL13 is implicated in germinal center formation by B lymphocytes and follicular helper T lymphocytes (TFH), and likely in their recruitment into the inflamed synovial tissues in RA, where they may contribute to pathogenesis by generating local immune responses and antibody production. Immunoglobulin G (IgG)-containing immune complexes stimulate TNF production by monocytes via direct activation of Fc gamma receptor III (FcγRIII), as reported in Cooper et al. (2012) PLoS One.; 7(1), hereby incorporated by reference in its entirety. It was reported in Jones et al. (2014) Arthritis Res. Ther.; 16(2):R10 and Bugatti et al. (2014) Rheumatology (Oxford); 53(1); 1886-95 that CXCL13 was higher in seropositive RA patients than in seronegative RA patients, consistent with Example 1 infra, both references hereby incorporated by reference in their entireties. CXCL13 is associated with severe RA with persistent ultrasonographic synovitis despite non-biologic DMARDs therapy, as reported in Bugatti et al. (2012) Arthritis Res. Ther.; 14(1): R34, hereby incorporated by reference in its entirety. Notably, there have been inconsistent reports on the roles of CXCL13 as a predictive marker for the response to TNF inhibitor in RA patients. In Greisen et al. (2014), Arthritis Res. Ther.; 16(5):434, baseline CXCL13 levels in early RA patients were inversely correlated with disease activity at 12 months after DMARDs and adalimumab therapy, which is consistent with Example 1 infra, hereby incorporated by reference in its entirety. Although Greisen et al. showed high baseline CXCL13 levels were generally associated with low disease activity after treatment with TNF inhibitors or DMARDs for 2 years, Greisen et al. did not assess whether baseline serum CXCL13 levels predicted the therapeutic response to TNF inhibitors. In contrast to the conclusion in Greisen et al., Dennis et al. (2014) Arthritis Res. Ther.; 16(2):R90 reported that CXCL13 was associated with lower ACR50 response rate to adalimumab and higher ACR50 response rate to tocilizumab, an IL-6 receptor inhibitor, after 24 weeks of therapy, hereby incorporated by reference in its entirety. Dennis et al. was a post hoc analysis of ADalimumab ACTemrA (ADACTA) trial results where tocilizumab monotherapy and adalimumab monotherapy were compared, described in Gabay et al. (2013) Lancet.; 381(9877): 1541-50, hereby incorporated by reference in its entirety. ROC analysis in Dennis et al. showed CXCL13 had only modest predictive ability with an AUC of 0.6. Notably, as opposed to the ADACTA trial, all but one patient in the study described in Example 1 infra were continued on baseline methotrexate and other DMARDs while taking TNF inhibitor. Furthermore, baseline CXCL13 and CXCL10 levels were highly correlated with each other in Example 1, and CXCL13 levels decreased after TNF inhibitor therapy only in responders.

As used herein, "DAS" refers to "disease activity score." In particular "DAS28" refers to a measure of disease activity in rheumatoid arthritis. The 28 refers to the 28 joints that are examined in the assessment. DAS28 is a composite score derived from measurements of swollen joints, tender joints, a measurement of erythrocyte sedimentation rate (ESR) or C reactive protein (CRP), and a global assessment of health.

As used herein, "DMARDS" refers to "disease-modifying antirheumatic drugs." DMARDS primarily work by blocking inflammation. While DMARDS typically do not comprise non-steroidal anti-inflammatory drugs (NSAIDS) or corticosteroids, they are often co-administered with such in order to help with pain and/or inflammation. Traditional DMARDS may include, for example, hydroxychloroquine sulfate, leflunomide, methotrexate, sulfasalazine, and other small molecules.

As used herein, the terms "effective amount" or "therapeutically effective amount" refer to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

As used herein, "etanercept" refers to the FDA-approved fusion protein that specifically binds to tumor necrosis factor (TNF), as well as any biosimilar compounds comprising a TNF receptor fused to the constant region of an IgG1 antibody, for example, but not limited to, etanercept-szzs. Etanercept acts as a decoy receptor for TNF. Use of etanercept to treat rheumatoid arthritis is described in, for example, Haraoui et al. (2007) Ther Clin Risk Manag.; 3(1): 99-105, hereby incorporated by reference in its entirety.

As used herein, "golimumab" refers to the FDA-approved human monoclonal antibody that specifically binds to tumor necrosis factor (TNF), as well as any biosimilar monoclonal antibodies or antigen-binding portions thereof. Golimumbab was originally isolated from a hybridoma clone produced by transgenic mice immunized with human TNFα. Use of goliumumab to treat rheumatoid arthritis is described in, for example, Smolen et al. (2009) Lancet; 374(9865) 210-221, hereby incorporated by reference in its entirety.

As used herein, "infliximab" refers to the FDA-approved chimeric monoclonal antibody that specifically binds to tumor necrosis factor (TNF), as well as any biosimilar monoclonal antibodies or antigen-binding portions thereof, including but not limited to, infliximab-dyyb. Infliximab was the first monoclonal antibody to TNF developed for treating rheumatoid arthritis. Infliximab is a chimeric human-mouse IgG monoclonal antibody. Use of infliximab to treat rheumatoid arthritis is described in, for example, Perdriger A. (2009) Biologics; 3: 183-191, hereby incorporated by reference in its entirety.

As used herein, the term "patient" refers to a biological system to which a treatment can be administered. A biological system can include, for example, an individual cell, a set of cells (e.g., a cell culture), an organ, a tissue, or a multi-cellular organism. A "patient" can refer to a human patient or a non-human patient, e.g. a mammalian or a non-mammalian patient.

As used herein, "TNF" refers to "tumor necrosis factor", also known as "TNFα", "TNF alpha" or occasionally "cachectin". TNF is a cytokine and a type II transmembrane protein that has a wide range of known biological activities in vivo.

As used herein, "TNF inhibitor" or "TNF inhibitors" refer to compositions which when administered to a patient reduce the biological activity of TNF in vivo. Several exemplary TNF inhibitors are described in Simsek I. (2010) Bull. NYU Hosp. Jt. Dis.; 68(3):204-10, hereby incorporated by reference in its entirety. TNF inhibitors include, but are not limited to, compositions which specifically bind to TNF and/or prevent TNF from interacting with its target receptor. Specific examples of TNF inhibitors include, but are not limited to, adalimumab, including (but not limited to) adalimumab-atto, certolizumab, etanercept, including (but not limited to) etanercept-szzs, golimumab, and infliximab, including (but not limited to) infliximab-dyyb.

As used herein, the terms "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder. For example, in the case of rheumatoid arthritis (RA), "preventing" or "preventing" may arise in a situation where a course of treatment is advanced in order to prevent or delay onset of new RA symptoms prior to their onset or appearance. In addition, "treating" or "treatment" does not require complete alleviation of signs or symptoms, does not require a cure, and specifically includes protocols that have only a marginal effect on the patient.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference in their entireties.

As used herein and in the appended claims, the singular forms "a", "and" and "the" include plural references unless the context clearly dictates otherwise.

The following non-limiting examples further illustrate certain aspects of the disclosure.

EXAMPLES

1. CXCL10 and CXCL13 Levels are Predictive Biomarkers for Tumor Necrosis Factor (TNF) Inhibitor Therapy in Rheumatoid Arthritis Patients Example 1 indicated that patient serum levels of CXCL10 and CXCL13 are valuable predictive biomarkers of response to TNF inhibitor therapy in patients suffering from rheumatoid arthritis (RA). Elevated baseline levels of CXCL10 and CXCL13 were associated with favorable response to TNF inhibitor therapy.

Materials and Methods

Patients and Assessment:

Patients with RA who met the inclusion and exclusion criteria were recruited during routine care in the rheumatology clinics at the Cooper University Hospital (Camden, N.J., USA). The inclusion criteria for this study were:

1. diagnosis of RA by American College of Rheumatology (ACR) criteria;
2. active RA defined by disease activity score (DAS) >4.4;
3. inadequate response to methotrexate; and
4. clinical indication for initiating adalimumab or etanercept treatment.

The exclusion criteria were:

1. diagnosis of other connective tissue diseases including systemic lupus erythematosus, systemic sclerosis, or dermatomyositis, or interstitial lung disease;
2. diagnosis of chronic infection including viral hepatitis or human immunodeficiency virus; and
3 history of malignancy.

All 29 patients except one were continued on baseline methotrexate and other DMARDs while taking adalimumab (twenty-two (22) patients) or etanercept (seven (7) patients). The patients were assessed and peripheral blood samples were obtained at baseline and fourteen (14) weeks after TNF inhibitor therapy. The results of rheumatoid factor (RF), anti-cyclic citrullinated peptide antibody (anti-CCP), and erythrocyte sedimentation rate (ESR) tests were obtained as part of patient care. Responders were defined as patients who had good to moderate response at week fourteen (14) by European League Against Rheumatism (EULAR) response criteria (fourteen (14) with adalimumab and two (2) with etanercept treatment), and non-responders were defined as having no response (eight (8) with adalimumab and five (5) with etanercept treatment). The research protocol was approved by the Institutional Review Board of Cooper University Hospital and all patients provided written informed consent for participation in the study.

Measurement of Chemokine Levels:

Freshly isolated serum samples were aliquoted and stored in a −80° C. freezer until use. Commercially available enzyme-linked immunosorbent assay (ELISA) kits were used for serum measurements of CXCL10 (R&D, Minneapolis, Minn., USA), CXCL13 (Sigma-Aldrich, St Louis, Mo., USA), and CCL20 (Sigma-Aldrich, St Louis, Mo., USA).

Statistical Analyses:

Statistical analyses were performed using SAS v9.4 (SAS Institute, Cary, N.C., USA), and graphs were generated using GraphPad Prism 6.0 (GraphPad Software, La Jolla, Calif., USA). Continuous variables were compared using Wilcoxon ranked sum test, and dichotomous variables were compared using Fisher's exact test. Correlations between pairs of continuous variables were performed using Spearman correlation coefficient. Differences between pretreatment and post-treatment chemokine levels were compared using analysis of variance (ANOVA) for repeated measures. Receiver operating characteristic (ROC) curve analysis was performed to assess the predictive ability of cytokine variables. In all the tests, a two-sided p value <0.05 was considered significant.

Results

Baseline Serum CXCL10 and CXCL13 Levels are Higher in Responders to TNF Inhibitor Therapy Twenty-nine (29) rheumatoid arthritis (RA) patients who were about to start either adalimumab or etanercept after having an inadequate response to methotrexate and other DMARDs were recruited. Five (5) patients had been treated with a TNF inhibitor previously, and their last treatment was at least three (3) months ago. After fourteen (14) weeks of TNF inhibitor therapy, using EULAR response criteria, the patients were classified into sixteen (16) good and moderate responders (collectively termed hereafter as 'responders') and thirteen (13) non-responders. Their baseline characteristics, summarized in TABLE 1 below, showed no significant differences between responders and non-responders. Values in TABLE 1 are presented as mean with standard deviation. P values were determined by Wilcoxon ranked sum test[a] and by Fisher's exact test[b].

TABLE 1

Baseline characteristics of rheumatoid arthritis patients.

| | Responders (n = 16) | Non-responders (n = 13) | p value |
|---|---|---|---|
| Age (years) | 51.6 ± 12.7 | 50.7 ± 8.1 | 0.80[a] |
| Gender (female %) | 69 (11/16) | 77 (10/13) | 0.70[b] |
| Duration (years) | 6.5 ± 4.9 | 7.4 ± 7.5 | 0.66[a] |
| RF or anti-CCP positive (%) | 75 (12/16) | 54 (7/13) | 0.27[b] |
| DAS28 ESR | 6.2 ± 1.1 | 6.7 ± 0.6 | 0.15[a] |
| ESR (mm) | 37 ± 31 | 30 ± 22 | 0.79[a] |

Figure 2A:
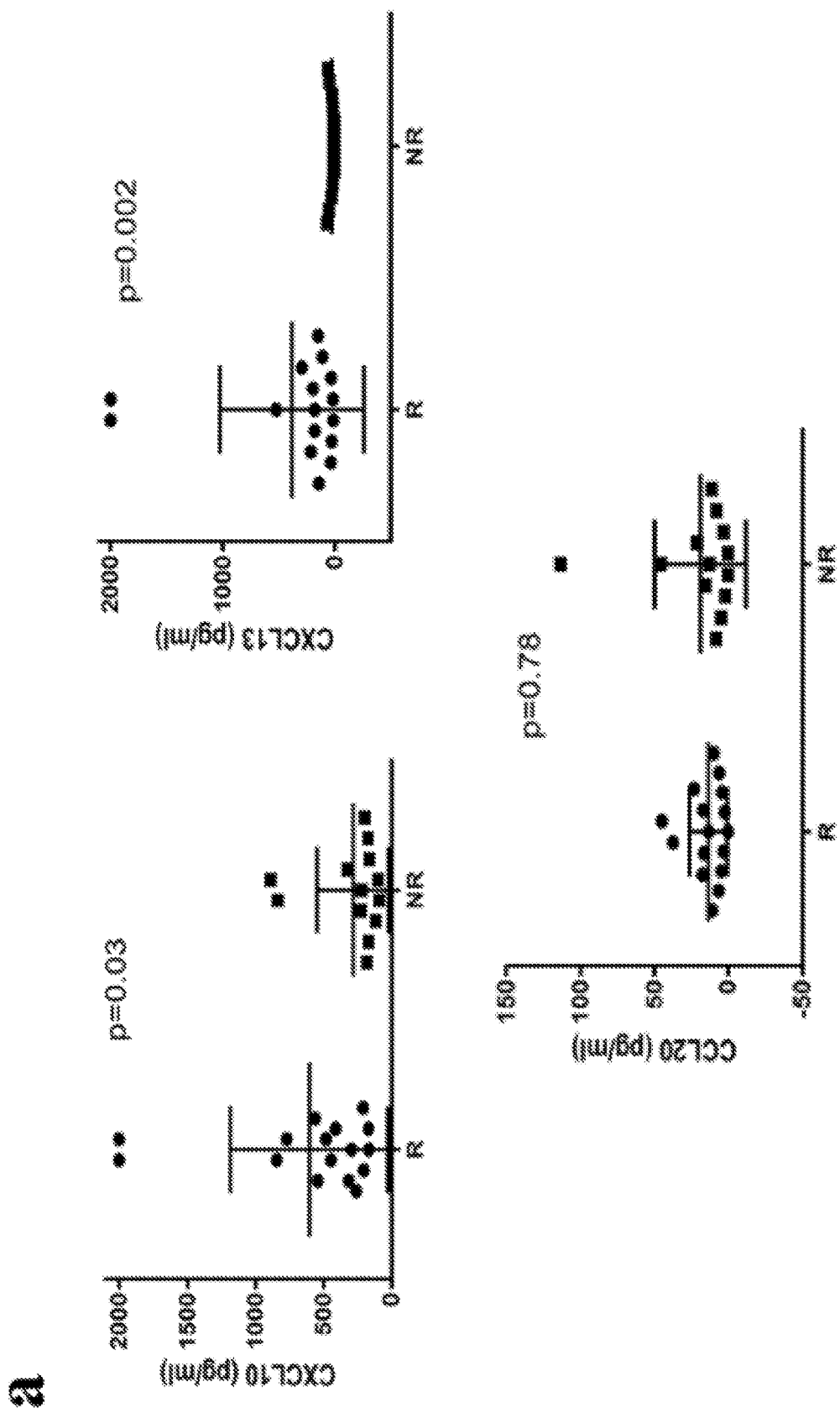
FIG. 2A represents that CXCL10 (p=0.03) and CXCL13 (p=0.002) levels were higher in responders than in non-responders. The chemokine levels in the two groups were compared using Wilcoxon ranked sum test. Bars represent mean±standard deviation. R responders, NR non-responders.

Baseline chemokine levels were measured by ELISA before starting TNF inhibitor therapy and compared between responders and non-responders (FIG. 2A). Responders had significantly higher serum levels of CXCL10 (606±581 vs 283±265 pg/mL, p=0.03) and CXCL13 (383±644 vs 27±24 pg/mL, p=0.002) compared to non-responders. There was no significant difference in CCL20 levels between responders and non-responders (14±13 vs 19±31 pg/mL, p=0.78).

Among patients who were treated with adalimumab (n=22), baseline CXCL10 and CXCL13 levels were higher in responders than in non-responders (p=0.02 and p=0.04 respectively). Among patients who were treated with etanercept (n=7), CXCL13 levels were higher in responders (p=0.045), and CXCL10 levels were numerically higher in responders, but the difference did not reach statistical significance (p=0.20).

Figure 2B:
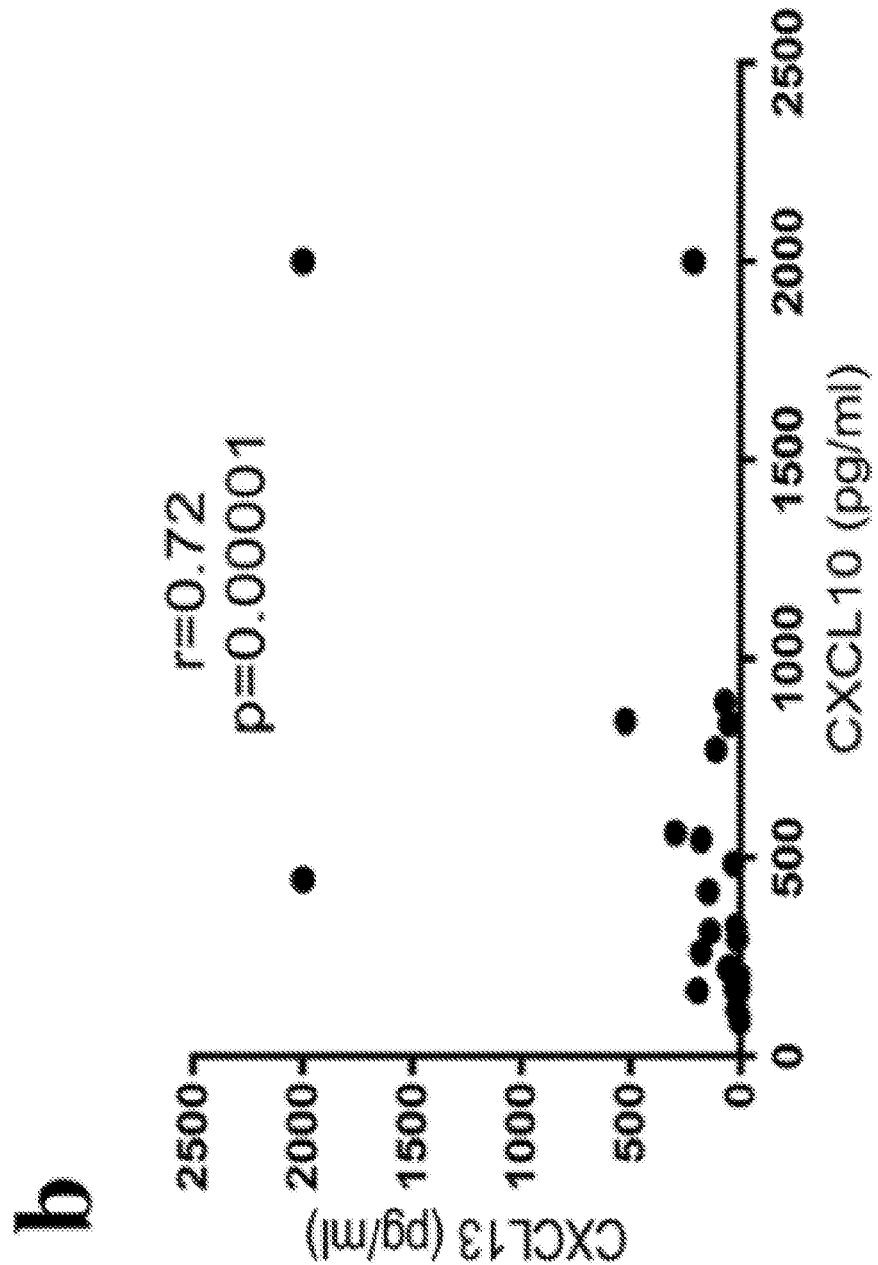
FIG. 2B represents correlation between baseline CXCL10 and CXCL13 levels. Baseline CXCL10 and CXCL13 levels were highly correlated (r=0.72, p=0.00001). The association between the two chemokine levels was assessed using Spearman correlation.

CXCL10 and CXCL13 Levels are Correlated with Each Other and are Higher in Seropositive RA Patients The relationship between chemokine levels and disease activity was assessed. Baseline or post-treatment levels of CXCL10, CXCL13, or CCL20 were not correlated with DAS28 or ESR. Baseline and post-treatment levels of CXCL10 and CXCL13 were correlated with each other (r=0.72, p=0.00001 and r=0.59, p=0.001 respectively) (FIG. 2B).

Chemokine levels were compared between seropositive and seronegative patients. Baseline CXCL10 and CXCL13 levels were higher in anti-CCP-positive patients than in anti-CCP-negative patients (p=0.02 and p=0.005 respectively). Baseline CXCL13 levels were higher in RF-positive patients than in RF-negative patients (p=0.02) (TABLE 2 below). There were no significant differences in post-treatment CXCL10 and CXCL13 levels between RF-positive and RF-negative patients (p=0.57 and p=0.72 respectively), and anti-CCP-positive and anti-CCP-negative patients (p=0.09 and p=0.21 respectively). Values in TABLE 2 are presented as mean with standard deviation. P values were determined by Wilcoxon ranked sum test. An * indicates p<0.05.

TABLE 2

Baseline chemokine levels in seropositive and seronegative RA patients.

|  | IgM RF+ (n = 16) | IgM RF− (n = 13) | p value |
|---|---|---|---|
| CXCL10 (pg/mL) | 510.2 ± 465.2 | 400.4 ± 525.3 | 0.16 |
| CXCL13 (pg/mL) | 371.6 ± 649.0 | 40.3 ± 55.6 | 0.02* |
| CXCL20 (pg/mL) | 9.7 ± 10.3 | 23.8 ± 30.5 | 0.09 |
|  | Anti-CCP+ (n = 15) | Anti-CCP− (n = 14) | p value |
| CXCL10 (pg/mL) | 557.3 ± 458.0 | 357.8 ± 512.9 | 0.02* |
| CXCL13 (pg/mL) | 396.6 ± 663.8 | 37.2 ± 54.4 | 0.005* |
| CXCL20 (pg/mL) | 9.6 ± 9.9 | 22.9 ± 29.7 | 0.12 |

CXCL10 and CXCL13 Levels Decrease after TNF Inhibitor Therapy in Responders

Post-treatment chemokine levels at fourteen (14) weeks after TNF inhibitor therapy were measured and compared to pretreatment (baseline) levels (TABLE 3 below). In responders, CXCL10, CXCL13, and CCL20 levels were decreased after TNF inhibitor therapy (p=0.01, p=0.0001, and p=0.003 respectively). In non-responders, CXCL13 levels did not change (p=0.86) and CXCL10 and CCL20 levels were decreased (p=0.04 and p=0.047 respectively). The percentage change was compared between responders and non-responders. CXCL13 levels were decreased by 62% of baseline levels after TNF inhibitor therapy in responders, and increased by 6% in non-responders (p=0.08). There was no difference in the percentage change of CXCL10 and CCL20 between responders and non-responders. P values in TABLE 3 were determined by analysis of variance (ANOVA) for repeated measures. An * indicates p<0.05.

TABLE 3

Pre-treatment (baseline) and post-treatment chemokine levels in responders and non-responders.

|  | Responders | | Non-responders | |
|---|---|---|---|---|
|  | Mean ± S.D. | p value | Mean ± S.D. | p value |
| CXCL10 (pg/mL) | | | | |
| Pre-treatment | 605.5 ± 580.6 | 0.01* | 283.2 ± 265.1 | 0.04* |
| Post-treatment | 411.1 ± 458.3 |  | 218.4 ± 237.3 |  |
| CXCL13 (pg/mL) | | | | |
| Pre-treatment | 382.7 ± 644.3 | <0.0001* | 26.7 ± 23.8 | 0.86* |
| Post-treatment | 90.6 ± 128.2 |  | 35.7 ± 46.8 |  |
| CCL20 (pg/mL) | | | | |
| Pre-treatment | 13.6 ± 12.7 | 0.003* | 19.0 ± 31.0 | 0.047* |
| Post-treatment | 6.9 ± 8.9 |  | 7.2 ± 7.2 |  |

Baseline CXCL10 and CXCL13 Levels Predict Response to TNF Inhibitor Therapy

RA patients were then classified into four groups:
1) high CXCL10/high CXCL13
2) high CXCL10/low CXCL13
3) low CXCL10/high CXCL13 and
4) low CXCL10/low CXCL13

These were based on baseline CXCL10 and CXCL13 cutoffs defined by their median values (260 pg/mL and 50 pg/mL respectively), and their response to TNF inhibitor therapy was compared. Ten (10) out of twelve (12) patients in the high CXCL10/high CXCL13 group were responders, and nine (9) out of twelve (12) patients in the low CXCL10/low CXCL13 group were non-responders.

Figure 3A:
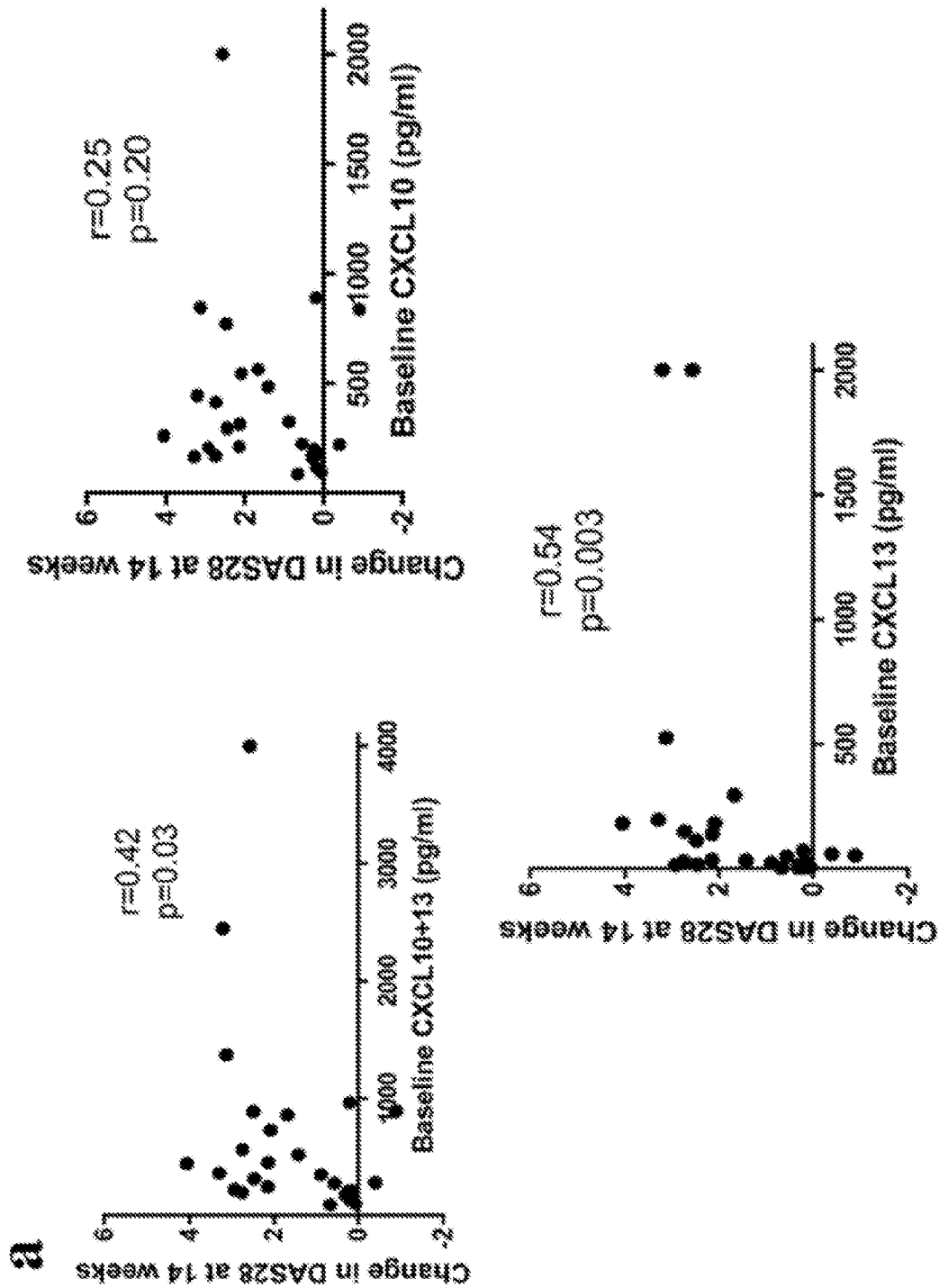
FIG. 3A represents correlation between baseline CXCL10+CXCL13, CXCL10, CXCL13 and change in DAS28 at 14 weeks after TNF inhibitor therapy. Baseline CXCL10+13 (r=0.42, p=0.03) and CXCL13 (r=0.54, p=0.003) were correlated with change in DAS28 at 14 weeks. The associations between chemokine levels and change in DAS28 were assessed using Spearman correlation.
Figure 3B:
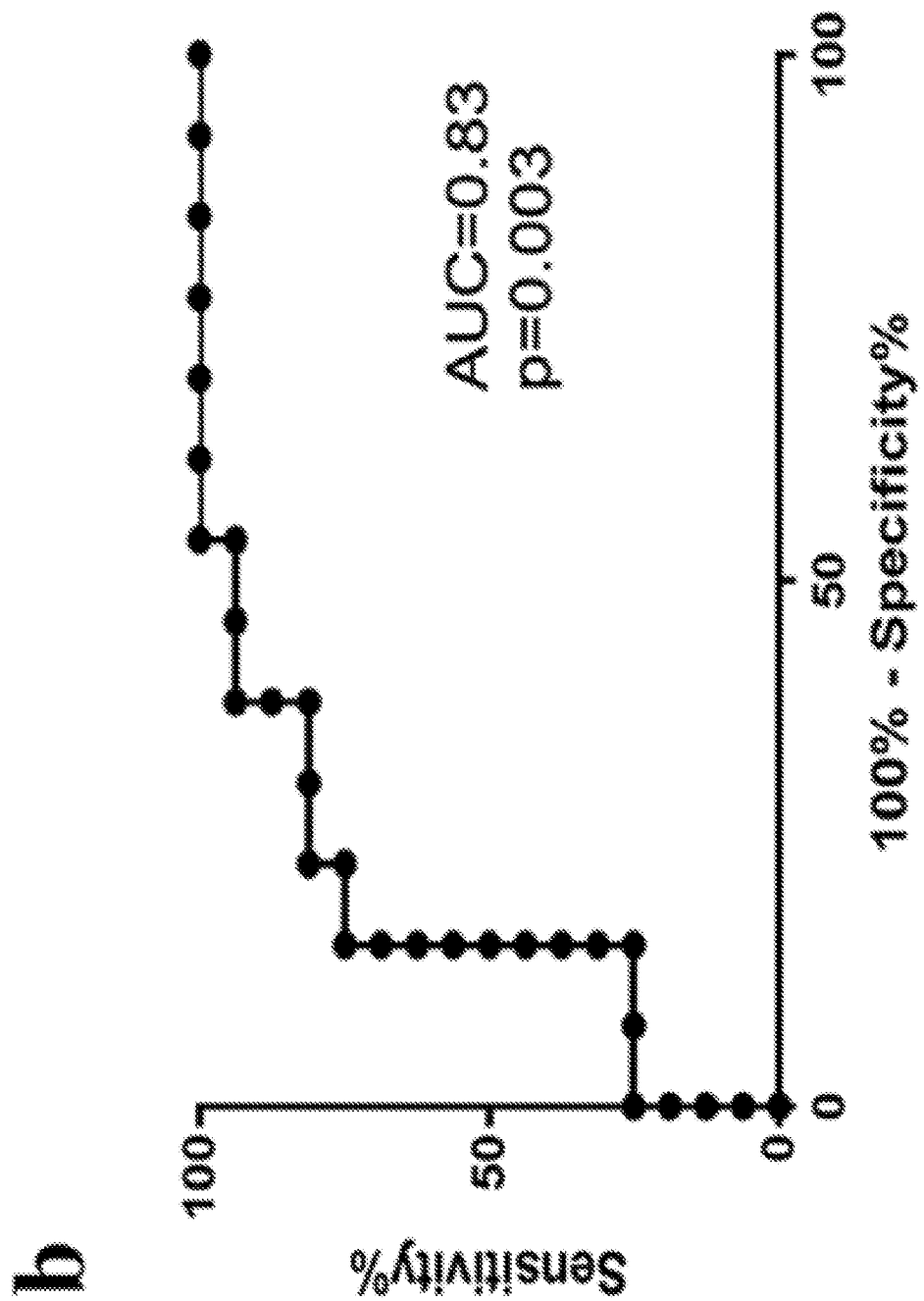
FIG. 3B represents predictive ability of CXCL10+CXCL13 for the response to TNF inhibitor therapy at fourteen (14) weeks. Area under the curve (AUC) in ROC curve analysis is 0.83.

A chemokine score, CXCL10+CXCL13, was created by simply adding baseline CXCL10 and CXCL13 levels. There was a significant difference in baseline CXCL10+CXCL13 between responders and non-responders (988±1050 vs 310±283 pg/ml, p=0.006). Baseline CXCL10+CXCL13 and CXCL13 were correlated with changes in DAS28 at fourteen (14) weeks after TNF inhibitor therapy (r=0.42, p=0.03 and r=0.54, p=0.003 respectively), and CXCL10 levels were not correlated (r=0.25, p=0.20) (FIG. 3A). ROC curve analysis was performed to assess the predictive ability of CXCL10+CXCL13 for EULAR good or moderate response to TNF inhibitor therapy. CXCL10+13 showed significant predictive ability based on the area under the curve (AUC) of 0.83 (FIG. 3B).

The results of Example 1 thus indicated that baseline CXCL10 and CXCL13 levels are associated with favorable response to TNF inhibitor therapy in moderate to severe RA patients. When analyzed separately based on the TNF inhibitors patients received, the results were similar, except that the difference for CXCL10 in patients treated with etanercept was not statistically significant, presumably due to the low subject number in this group. All the patients included in this study had inadequate response to methotrexate and had high disease activity measured by DAS28 when starting TNF inhibitor therapy.

2. sCD27 Represents an Additional Predictive Biomarker for TNF Inhibitor Therapy in Rheumatoid Arthritis Patients Example 2 indicates that patient serum levels of sCD27 is a valuable predictive biomarker of response to TNF inhibitor therapy in patients suffering from rheumatoid arthritis (RA). Elevated baseline levels of sCD27 was associated with favorable response to TNF inhibitor therapy.

Materials and Methods

Patients and Assessment:

Patients with rheumatoid arthritis (RA) who met the inclusion and exclusion criteria were recruited during routine care in the rheumatology clinics at the Cooper University Hospital. Like in Example 1, the inclusion criteria for this study were:

1. diagnosis of RA by American College of Rheumatology (ACR) criteria;
2. active RA defined by Disease activity score (DAS) >4.4;
3. inadequate response to methotrexate; and
4. clinical indication for initiating adalimumab or etanercept treatment.

Also as in Example 1, the exclusion criteria were:

1. diagnosis of other connective tissue diseases including systemic lupus erythematosus, systemic sclerosis, or dermatomyositis, or interstitial lung disease;
2. diagnosis of chronic infection including viral hepatitis or HIV; or
3. history of malignancy.

All patients except one were continued on baseline methotrexate and other disease modifying anti-rheumatic drugs (DMARDs) while taking adalimumab or etanercept. Additionally healthy subjects were recruited. The patients were assessed and peripheral blood samples were obtained at baseline and fourteen (14) weeks after TNF inhibitor therapy. The results of rheumatoid factor (RF), anti-cyclic citrullinated peptide antibody (anti-CCP), and erythrocyte sedimentation rate (ESR) tests were obtained as part of patient care. Responders were defined as patients who had good to moderate response at week fourteen (14) by European League Against Rheumatism (EULAR) response criteria, and non-responders were defined as having no response. The research protocol was approved by the Institutional Review Board of Cooper University Hospital.

Measurement of sCD27 Levels:

Freshly isolated serum samples were aliquoted and stored in a −80° C. freezer until use. Commercially obtained enzyme-linked immunosorbent assay (ELISA) kits were used for serum measurements of sCD27 (eBioscience, San Diego, Calif., USA).

Statistical Analyses:

Statistical analyses were performed using SAS v9.4 (SAS Institute, Cary, N.C., USA), and graphs were generated using GraphPad Prism 6.0 (GraphPad Software, La Jolla, Calif., USA). Continuous variables were compared using Wilcoxon ranked sum test, and dichotomous variables were compared using Fisher's exact test. Receiver operating characteristic (ROC) curve analysis was performed to assess the predictive ability of cytokine variables. In all the tests, a two-sided p-value <0.05 was considered statistically significant.

Results

Twenty eight (28) rheumatoid arthritis (RA) patients who were about to start either adalimumab or etanercept after having an inadequate response to methotrexate and other other disease modifying anti-rheumatic drugs (DMARDs) were recruited. After 14 weeks of TNF inhibitor therapy, using EULAR response criteria, the patients were classified into 15 good and moderate responders (collectively termed hereafter as 'responders') and 13 non-responders. Their baseline characteristics including age, gender, disease duration and DAS scores showed no significant differences between responders and non-responders.

Baseline sCD27 levels were measured by ELISA before starting TNF inhibitor therapy and compared between responders and non-responders (FIG. 4). Responders had significantly higher serum levels of sCD27 compared to non-responders (119.9±26.3 vs. 88.8±29.8 U/mL, p=0.008). Both responder and non-responder RA groups had higher levels of sCD27 compared to healthy controls (p<0.0001 and p=0.0002 respectively).

ROC curve analysis was performed to assess the predictive ability of sCD27 for EULAR good or moderate response to TNF inhibitor therapy. sCD27 showed significant predictive ability based on the area under the curve (AUC) of 0.76 (p=0.02).

3. Further Statistical Analysis of CXCL10, CXCL13, and sCD27 Values

Materials and Methods:

For this analysis, CXCL10, CXCL13, and sCD27 values were normalized to the respective analyte mean values in the entire cohort, and the 3 normalized values for each patient were added to yield a "summative value." The overall mean of these summative values is 3, with a standard deviation of 3.04.

Diagnostic test evaluation was carried out using MEDCALC for the following test cut-offs:
  Mean of the summative values (3);
  Mean of the summative values−0.33 standard deviation (1.99);
  Mean of the summative values−0.5 standard deviation (1.48).

Definitions

For purposes of Examples 3 and 4, the following definitions, taken from MEDCALC, are used:
  a: true positives;
  b: false negatives;
  c: false positives; and
  d: true negatives.

"Sensitivity" is defined as the probability that a test result will be positive when the disease is present (true positive rate).

"Specificity" is defined as the probability that a test result will be negative when the disease is not present "Positive likelihood ratio" is defined as the ratio between the probability of a positive test result given the presence of the disease and the probability of a positive test result given the absence of the disease.

"Negative likelihood ratio" is defined as the ratio between the probability of a negative test result given the presence of the disease and the probability of a negative test result given the absence of the disease.

"Positive predictive value" is defined as the probability that the disease is present when the test is positive.

"Negative predictive value" is defined as the probability that the disease is not present when the test is negative.

Results:

The results of the diagnostic test evaluation are displayed in TABLE 4, TABLE 5, and TABLE 6 below. Sensitivity, specificity, positive and negative predictive value as well as disease prevalence are expressed as percentages. Confidence intervals for sensitivity and specificity are "exact" Clopper-Pearson confidence intervals. Confidence intervals for the likelihood ratios were calculated using the "Log method" as described on page 109 of Altman et al. (2000), Statistics with confidence, $2^{nd}$ ed. BMJ Books, hereby incorporated by reference in its entirety. Confidence intervals for the predictive values are the standard logic confidence intervals given by Mercaldo et al. (2007) Statistics in Medicine 26:2170-2183, hereby incorporated by reference in its entirety.

TABLE 4

Results for test cutoff equal to the mean of the summative value (i.e. above 3 for responders, below 3 for non-responders).

| Statistic | Formula | Value | 95% C.I. |
| --- | --- | --- | --- |
| Sensitivity | $\dfrac{a}{a+b}$ | 40.00% | 16.34% to 67.71% |
| Specificity | $\dfrac{d}{c+d}$ | 84.62% | 54.55% to 98.08% |
| Positive Likelihood Ratio | $\dfrac{\text{Sensitivity}}{100-\text{Specificity}}$ | 2.60 | 0.63 to 10.73 |
| Negative Likelihood Ratio | $\dfrac{100-\text{Sensitivity}}{\text{Specificity}}$ | 0.71 | 0.44 to 1.14 |
| Disease Prevalence | $\dfrac{a+b}{a+b+c+d}$ | 53.57 | 33.87% to 72.49% |
| Positive Predictive Value | $\dfrac{a}{a+c}$ | 75.00% | 42.09% to 92.53% |
| Negative Predictive Value | $\dfrac{d}{b+d}$ | 55.00% | 43.21% to 66.25% |

TABLE 5

Results for test cutoff equal to the mean of summative values - 0.33 standard deviation (1.99).

| Statistic | Formula | Value | 95% C.I. |
|---|---|---|---|
| Sensitivity | $\frac{a}{a+b}$ | 73.33% | 44.90% to 92.21% |
| Specificity | $\frac{d}{c+d}$ | 76.92% | 46.19% to 94.96% |
| Positive Likelihood Ratio | $\frac{\text{Sensitivity}}{100 - \text{Specificity}}$ | 3.18 | 1.13 to 8.98 |
| Negative Likelihood Ratio | $\frac{100 - \text{Sensitivity}}{\text{Specificity}}$ | 0.35 | 0.14 to 0.84 |
| Disease Prevalence | $\frac{a+b}{a+b+c+d}$ | 53.57% | 33.87% to 72.49% |
| Positive Predictive Value | $\frac{a}{a+c}$ | 78.57% | 56.49% to 91.19% |
| Negative Predictive Value | $\frac{d}{b+d}$ | 71.43% | 50.65% to 85.90% |

TABLE 6

Results for test cutoff equal to the mean of the summative values - 0.5 standard deviation (1.48).

| Statistic | Formula | Value | 95% C.I. |
|---|---|---|---|
| Sensitivity | $\frac{a}{a+b}$ | 100% | 78.20% to 100% |
| Specificity | $\frac{d}{c+d}$ | 53.85% | 25.13% to 80.78% |
| Positive Likelihood Ratio | $\frac{\text{Sensitivity}}{100 - \text{Specificity}}$ | 2.17 | 1.20 to 3.90 |
| Negative Likelihood Ratio | $\frac{100 - \text{Sensitivity}}{\text{Specificity}}$ | 0.00 | |
| Disease Prevalence | $\frac{a+b}{a+b+c+d}$ | 53.57% | 33.87% to 72.49% |
| Positive Predictive Value | $\frac{a}{a+c}$ | 71.43% | 58.15% to 81.81% |
| Negative Predictive Value | $\frac{d}{b+d}$ | 100% | |

4. Application of Serum Biomarker Levels in Therapeutic-Decision Making Process for Administration of TNF Inhibitor Therapy This Example considers three (3) scenarios of therapeutic decision-making approaches based on an analysis of combined baseline CXCL10, CXCL13, and sCD27 serum levels, using the reference population of RA patients described in Examples 1 and 2 supra. One of ordinary skill in the art will recognize the reference population and relative reference values may vary as additional reference samples are analyzed in future experimentation.

Biological samples containing CXCL10, CXCL13, and sCD27 are taken from each of patient 1, patient 2, and patient 3. The baseline levels of CXCL10, CXCL13, and sCD27 are established for each of patient 1, patient 2, and patient 3 through assaying the biological sample. The baseline level of each marker is normalized to the mean level of the same marker in the reference population (e.g. CXCL10 is normalized to the mean level of CXCL10 in the reference population), and the normalized value of each marker in each of patient 1, patient 2, and patient 3 are added to yield a combined "summative normalized level" for each of CXCL10, CXCL13, and sCD27. The predicted likelihood of response to therapy for the patient is calculated based on the sensitivity and specificity of the test at the patient's "summative normalized level". In this Example, the summative normalized level is weighed equally for each of CXCL10, CXCL13, and sCD27. Differential weighing of the markers may occur based on relative impact of each variable on the predictive power, depending on future experimentation. The results are indicated in TABLE 7 below.

TABLE 7

Evaluating likelihood of positive response to TNF inhibitor therapy in three different patients with three different levels of CXCL10, CXCL13, and sCD27.

| | Normalized level of CXCL10 | Normalized level of CXCL13 | Normalized level of sCD27 | Summative normalized level | Likelihood of positive response to TNF inhibitor therapy |
|---|---|---|---|---|---|
| Patient 1 | 1.1 | 0.95 | 0.95 | 3.0 | 75% |
| Patient 2 | 0.2 | 0.4 | 0.27 | 0.87 | 55.6% |
| Patient 3 | 1.5 | 1.6 | 1.1 | 4.2 | 100% |

What is claimed is:

1. A method of treating or ameliorating rheumatoid arthritis (RA) by predicting a therapeutic response to Tumor Necrosis Factor (TNF) inhibitor therapy in a patient, the method comprising:
   a) obtaining a biological sample from a patient diagnosed with RA,
   b) assaying said biological sample to determine baseline serum level(s) of at least one biomarker selected from the group consisting of C-X-C Motif Chemokine Ligand 10 (CXCL10) and C-X-C Motif Chemokine Ligand 13 (CXCL13) for said patient,
   c) comparing said baseline serum level(s) of said at least one biomarker with reference serum level(s) of said at least one biomarker generated from a population of individuals diagnosed with RA,
      wherein, if for said patient said baseline serum level(s) of said at least one biomarker is(are) elevated relative to said reference serum level(s) of said at least one biomarker, said patient is identified as being a candidate for TNF inhibitor therapy, and
   d) administering to said patient a therapeutically effective amount of a TNF inhibitor, if for said patient said baseline serum level(s) of said at least one biomarker is(are) elevated relative to said reference serum level(s) of said at least one biomarker,
   wherein said TNF inhibitor is selected from the group consisting of adalimumab and antigen-binding portions thereof, certolizumab and antigen-binding portions thereof, etanercept, golimumab and antigen-binding portions thereof, infliximab and antigen-binding portions thereof, and any combinations thereof.

2. The method of claim 1, further comprising assaying said biological sample to determine a baseline serum level of soluble CD27 (sCD27) and comparing said baseline serum level of sCD27 with a reference serum level of sCD27 generated from a population of individuals diagnosed with RA.

3. The method of claim 1, wherein assaying the biological sample comprises one of the following:
   (a) contacting the biological sample with at least one antibody selected from the group consisting of an anti-CXCL10 antibody and an anti-CXCL13 antibody, and
       detecting binding between said at least one antibody and said at least one biomarker;
   or
   (b) contacting the biological sample with at least one antibody selected from the group consisting of an anti-CXCL10 antibody and an anti-CXCL13 antibody,
       further contacting the biological sample with an anti-IgG antibody, and
       detecting binding of said anti-IgG antibody with said at least one antibody.

4. The method of claim 2, wherein assaying the biological sample comprises one of the following:
   (a) contacting the biological sample with an anti-CD27 antibody and
       detecting binding between said anti-CD27 antibody and sCD27;
   or
   (b) i contacting the biological sample with an anti-CD27 antibody,
       further contacting the biological sample with an anti-IgG antibody, and
       detecting binding of said anti-IgG antibody with said anti-CD27 antibody.

5. The method of claim 1, further comprising administering to said patient a disease-modifying antirheumatic drug (DMARD), wherein said DMARD is selected from the group consisting of hydroxychloroquine sulfate, leflunomide, methotrexate, sulfasalazine, and any combinations thereof.

6. A method of treating or ameliorating rheumatoid arthritis (RA) by predicting a therapeutic response to Tumor Necrosis Factor (TNF) inhibitor therapy in a patient, the method comprising:
   a) obtaining a biological sample from a patient diagnosed with RA,
   b) assaying the biological sample to determine a baseline serum level of soluble CD27 (sCD27) for said patient,
   c) comparing said baseline serum level of sCD27 with a reference serum level of sCD27 generated from a population of individuals diagnosed with RA,
      wherein, if for said patient said baseline serum level of sCD27 is elevated relative to said reference serum level of sCD27, said patient is identified as being a candidate for TNF inhibitor therapy, and
   d) administering to said patient a therapeutically effective amount of a TNF inhibitor, if for said patient said baseline serum level of sCD27 is elevated relative to said reference serum level of sCD27,
   wherein said TNF inhibitor is selected from the group consisting of adalimumab and antigen-binding portions thereof, certolizumab and antigen-binding portions thereof, etanercept, golimumab and antigen-binding portions thereof, infliximab and antigen-binding portions thereof, and any combinations thereof.

7. The method of claim 6, wherein assaying the biological sample comprises one of the following:
   (a) contacting the biological sample with an anti-CD27 antibody and
       detecting binding between said anti-CD27 antibody and sCD27;
   or
   (b) contacting the biological sample with an anti-CD27 antibody,
       further contacting the biological sample with an anti-IgG antibody, and
       detecting binding of said anti-IgG antibody with said anti-CD27 antibody.

8. A method of treating or ameliorating rheumatoid arthritis (RA) by measuring a therapeutic response to Tumor Necrosis Factor (TNF) inhibitor therapy in a patient, the method comprising
   a) obtaining a first biological sample from a patient diagnosed with RA prior to starting a TNF inhibitor therapy,
   b) assaying the first biological sample to determine baseline serum level(s) of at least one biomarker selected from the group consisting of CXCL10 and CXCL13 for said patient,
   c) administering a therapeutically effective amount of a TNF inhibitor to said patient for a period of time ranging from about 1 month to about 24 months, d) obtaining a second biological sample from the patient after said period of time, e) assaying the second biological sample to determine treatment serum level(s) of said at least one biomarker for said patient, f) comparing said baseline serum level(s) of said at least one biomarker with said treatment serum level(s) of said at least one biomarker, and g) continuing administration of said TNF inhibitor to said patient if said baseline serum level(s) of said at least one biomarker is(are) elevated relative to said treatment serum level(s) of said at least one biomarker, and suspending administration of said TNF inhibitor to said patient if said baseline serum level(s) of said at least one biomarker is(are) not elevated relative to said treatment serum level(s) of said at least one biomarker, wherein said TNF inhibitor is selected from the group consisting of adalimumab and antigen-binding portions thereof, certolizumab and antigen-binding portions thereof, etanercept, golimumab and antigen-binding portions thereof, infliximab and antigen-binding portions thereof, and any combinations thereof.

9. The method of claim 8, further comprising assaying the first biological sample to determine a baseline serum level of soluble CD27 (sCD27), assaying the second biological sample to determine a treatment serum level of sCD27, and comparing said baseline serum level of sCD27 with said treatment serum level of sCD27.

10. The method of claim 8, wherein assaying the first or second biological sample comprises one of the following:
  (a) contacting the first or second biological sample with at least one antibody selected from the group consisting of an anti-CXCL10 antibody and an anti-CXCL13 antibody and
    detecting binding between said at least one antibody and said at least one biomarker;
  or
  (b) contacting the first or second biological sample with at least one antibody selected from the group consisting of an anti-CXCL10 antibody and an anti-CXCL13 antibody,
    contacting the biological sample with an anti-IgG antibody, and
    detecting binding of said anti-IgG antibody with said at least one antibody.

11. The method of claim 9, wherein assaying the first or second biological sample comprises
  contacting the first or second biological sample with an anti-CD27 antibody, and
  detecting binding between said anti-CD27 antibody and sCD27.

12. The method of claim 8, wherein assaying the first or second biological sample comprises
  contacting the first or second biological sample with at least one antibody selected from the group consisting of an anti-CXCL10 antibody and an anti-CXCL13 antibody,
  further contacting the biological sample with an anti-IgG antibody, and
  detecting binding of said anti-IgG antibody with said at least one antibody.

13. A method of treating or ameliorating rheumatoid arthritis (RA) using a Tumor Necrosis Factor (TNF) inhibitor by measuring a therapeutic response to TNF inhibitor therapy in a patient, the method comprising
  a) obtaining a first biological sample from a patient diagnosed with rheumatoid arthritis (RA) prior to starting a TNF inhibitor therapy,
  b) assaying the first biological sample to determine a baseline serum level of soluble CD27 (sCD27) for said patient,
  c) administering a TNF inhibitor to said patient for a period of time ranging from about 1 month to about 24 months,
  d) obtaining a second biological sample from the patient after said period of time, e) assaying the second biological sample to determine a treatment serum level of sCD27 for said patient,
  f) comparing said baseline serum level of sCD27 with said treatment serum level of sCD27, and
  g) continuing administration of said TNF inhibitor to said patient if said baseline serum level of sCD27 is elevated relative to said treatment serum level of sCD27, and suspending administration of said TNF inhibitor to said patient if said baseline serum level of sCD27 is not elevated relative to said treatment serum level of sCD27,
  wherein said TNF inhibitor is selected from the group consisting of adalimumab and antigen-binding portions thereof, certolizumab and antigen-binding portions thereof, etanercept, golimumab and antigen-binding portions thereof, infliximab and antigen-binding portions thereof, and any combinations thereof.

14. The method of claim 13, wherein assaying the first or second biological sample comprises one of the following:
  (a) contacting the first or second biological sample with an anti-CD27 antibody and
    detecting binding between said anti-CD27 antibody and sCD27;
  or
  (b) contacting the first or second biological sample with an anti-CD27 antibody,
    contacting the biological sample with an anti-IgG antibody, and
    detecting binding between said anti-IgG antibody with said anti-CD27 antibody.

* * * * *